US007566332B2

(12) United States Patent
Jarrard et al.

(10) Patent No.: US 7,566,332 B2
(45) Date of Patent: Jul. 28, 2009

(54) METHODS AND APPARATUS FOR DISPERSING CURRENT FLOW IN ELECTROSURGERY

(75) Inventors: Jerry W. Jarrard, Sunnyvale, CA (US); Robert S. Behl, Palo Alto, CA (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 971 days.

(21) Appl. No.: 10/705,166

(22) Filed: Nov. 6, 2003

(65) Prior Publication Data
US 2005/0101947 A1 May 12, 2005

(51) Int. Cl.
*A61B 18/18* (2006.01)
(52) U.S. Cl. .............................. 606/35; 606/32; 606/38
(58) Field of Classification Search ............. 606/27–34, 606/35–40, 41–50; 607/96, 98, 99–103, 607/105, 113
See application file for complete search history.

(56) References Cited

U.S. PATENT DOCUMENTS

| 3,683,923 | A | * | 8/1972 | Anderson .................... 606/35 |
| 4,416,276 | A | | 11/1983 | Newton et al. |
| 4,754,757 | A | | 7/1988 | Feucht |
| 4,844,063 | A | * | 7/1989 | Clark ........................... 606/39 |
| 5,868,740 | A | | 2/1999 | LeVeen et al. |
| 6,050,992 | A | | 4/2000 | Nichols |
| 6,337,998 | B1 | | 1/2002 | Behl et al. |
| 6,796,980 | B2 | * | 9/2004 | Hall ............................ 606/34 |
| 6,860,881 | B2 | * | 3/2005 | Sturm et al. .................. 606/35 |

OTHER PUBLICATIONS

PCT International Search Report for PCT/US2004/036250, Applicant: Scimed Life Systems, Inc., Forms PCT/ISA/210 and 220, dated Mar. 10, 2005 (6 pages).
PCT Written Opinion of the International Search Authority for PCT/US2004/036250, Applicant: Scimed Life Systems, Inc., Form PCT/ISA/237, dated Mar. 10, 2005 (5 pages).

* cited by examiner

*Primary Examiner*—Lee S Cohen
(74) *Attorney, Agent, or Firm*—Vista IP Law Group LLP

(57) ABSTRACT

Methods and apparatus for delivering, monitoring, balancing, and/or dispersing high-frequency current flow in monopolar electrosurgery. The methods generally include positioning an active electrode in or on target tissue, positioning at least two dispersive electrodes on tissue remote from the target tissue, establishing electrical current flow from the active electrode through the dispersive electrodes, and individually adjusting the current through at least one of the dispersive electrodes to balance the current through the dispersive electrodes. By adjusting and balancing the current through two or more dispersive electrodes, safety of electrosurgical systems may be enhanced by preventing unwanted patient burns.

36 Claims, 6 Drawing Sheets

METHODS AND APPARATUS FOR DISPERSING CURRENT FLOW IN ELECTROSURGERY

FIELD OF INVENTION

The present invention relates to methods and apparatus for dispersing return current flow in monopolar electrosurgery.

BACKGROUND

Electrosurgery generally refers to surgery using electricity to achieve a certain effect at one or more target tissue sites in a patient. Typically, electrosurgery involves using high-frequency electrical energy, such as radio frequency (RF) energy, to cut or dessicate tissue, coagulate blood to stop bleeding from small blood vessels, cause tissue necrosis, and the like. For example, high-frequency electrical energy may be used with an electrosurgical scalpel to start or deepen an incision and/or to coagulate small blood vessels that are cut during incision. In another example, high-frequency energy may be delivered to diseased regions in target tissue, such as cancerous metastases in a liver, to cause necrosis of the diseased regions.

Equipment for performing electrosurgery generally includes a high-frequency electrical energy source, an active electrode, a dispersive electrode sometimes called a "return electrode"), and wiring for connecting the energy source to the active and dispersive electrodes. The high-frequency energy source generally supplies a high-frequency current to the active electrode, via the wiring, and the active electrode is generally used to apply the current at a target tissue site on a patient for performing an electrosurgical task. Typically, the active electrode is relatively small in surface area, relative to the dispersive electrode, so that relatively high current density is delivered by the active electrode. The high-frequency current travels from the active electrode, through the patient, to the dispersive electrode. Both the active and dispersive electrodes are attached to the energy source via one or more cables. Thus, a typical electrosurgery system may include an electrical circuit including an energy source, cable to active electrode, patient, dispersive electrode, and cable to energy source.

There are two general types of electrosurgical systems currently in use, namely bipolar and monopolar systems. In bipolar electrosurgery systems, both electrodes may be similar in surface area and are positioned in close proximity to one another, e.g., together on the same, handheld electrosurgical device. For example, some bipolar devices are configured as forceps (similar to tweezers) with the distal end of one prong of the forceps being a first active electrode and the distal end of the other prong being a second active electrode. Bipolar surgical systems are widely used for coagulating tissue, especially in procedures where it is important to prevent electric current from flowing through tissues adjacent to the target tissues.

Monopolar systems, however, are much more commonly used than bipolar systems. In monopolar electrosurgery, the active and dispersive electrodes are typically separated by a significantly greater distance than the electrodes in bipolar electrosurgery systems. Both electrodes are connected to a high-frequency energy generator. FIG. 1 schematically illustrates a monopolar electrosurgery system 100 that may include a high-frequency electrical energy source 102, an active electrode cable 104, an active electrode 106, a patient 112, a dispersive electrode 108, and a dispersive electrode cable 110.

In any type of electrosurgery, if a return electrode or other return path were not provided so that electrical current delivered to a patient by the active electrode could not readily return to the energy source to complete the circuit loop, the system would not work. Moreover, even if a return path is provided, current from an electrosurgical device may harm a patient if the return path is flawed in some way. When a return path malfunctions in monopolar electrosurgery, an unwanted patient burn may result. Patient burns at locations other than the target tissue site typically occur when current returning from the active electrode to the energy source becomes too concentrated (dense) at the location where the current leaves the patient. As described briefly above, a monopolar active electrode is typically relatively small, often only one or two millimeters (1-2 mm) or less in diameter at its operative, distal end. When current from an energy source is delivered to such a small device, a high current density is produced that can be used for ablation, coagulation, necrosis, and the like at the target site.

Dispersive electrodes, in contrast, are designed to have significantly larger surface areas. For example, a commonly used dispersive electrode is the Valleylab™ PolyHesive™ Patient Return Electrode, available from Valleylab (Boulder, Colo.), a division of Tyco Healthcare LP. A Valleylab™ PolyHesive™ Patient Return Electrode generally includes a thin, flexible, adhesive pad, measuring approximately seven inches by four inches (7"×4"), with an attached electrical cable for connecting to an RF energy source. The large surface area of such a patient return electrode, when compared to the surface area of the active electrode, causes current flowing out of the patient through the return electrode to have a relatively low current density. The low current density is intended to prevent excessive heating or burning of the patient's skin at the return electrode/skin interface.

Generally, dispersive electrodes for monopolar electrosurgery (also referred to as "patient return electrodes", "return pads" or simply "pads") work sufficiently well to disperse current and return it from a patient to a generator. Occasionally, however, a dispersive pad may malfunction, causing high density current at the dispersive pad/patient interface and possibly a patient burn. For example, the wiring of a dispersive pad may malfunction, a dispersive pad may be improperly placed so that it contacts the patient with a smaller surface area than intended, a dispersive pad may partially fall off the patient during a procedure, and the like.

The risk of unwanted patient burns in monopolar electrosurgery has become increasingly important as monopolar surgery devices have become increasingly more powerful. With the advent of active electrodes with larger surface areas, such as the LeVeen™ family of electrodes (distributed by Boston Scientific Medi-Tech, San Jose, Calif.), typical impedance loads for electrosurgery generators have decreased. A decreased load requires a generator to provide increased current in order to deliver a given amount of energy (watts). For example, the RF-2000™ and RF-3000™ Radiofrequency Generators (also distributed by Boston Scientific Medi-Tech) provide up to one hundred Watts (100 W) and two hundred Watts (200 W) of radio frequency energy, respectively.

High-current monopolar surgery devices may provide advantages in many electrosurgical procedures. A monopolar electrode, such as the LeVeen™ Needle Electrode or CoAccess™ Electrode (also available from Boston Scientific Medi-Tech), used with an RF-2000™ or RF-3000™ may be particularly advantageous for ablating and/or necrosing tissue in a cancerous tumor in a solid organ such as cancerous metastases in the liver.

Some currently available monopolar electrosurgery systems may include one or more safeguards against unwanted patient burns. For example, some systems may include multiple dispersive electrodes to disperse current from a patient. These systems represent an improvement over one-pad systems, but a risk still exists that current flowing through two or more dispersive electrodes on a patient may be unbalanced. Even if multiple pads are used to disperse current, a patient burn may still occur if current flowing to one pad is sufficiently high to cause such a burn.

Therefore, improved monopolar electrosurgical methods and apparatus would be useful.

SUMMARY OF THE INVENTION

The present invention is directed to methods and apparatus for delivering, monitoring, balancing, and/or dispersing high-frequency current in monopolar electrosurgery. In accordance with various aspects of the invention, the safety of electrosurgical systems may be enhanced by preventing unwanted patient burns.

In one aspect of the invention, a method for delivering high-frequency energy to a target site in human tissue may include positioning at least one active electrode in or on tissue at a target site, positioning at least two dispersive electrodes on tissue at sites remote from the target site, establishing high-frequency current flow between the active electrode and each of the dispersive electrodes, and individually adjusting the current through at least one of the dispersive electrodes to improve the balance of current through the dispersive electrodes.

In some embodiments, the method further includes monitoring resistance in each of the dispersive electrodes and comparing resistances in the dispersive electrodes to detect one or more dispersive electrodes having a higher resistance than one or more other dispersive electrodes. Optionally, the method may further include adding resistance to one or more dispersive electrodes that have lower resistances than one or more other dispersive electrodes. Alternatively, the method may involve repositioning at least one dispersive electrode on the tissue, wherein the at least one dispersive electrode has a higher resistance than at least one other dispersive electrode.

In some embodiments, the method may include monitoring current in each of the dispersive electrodes and comparing currents in the dispersive electrodes to one another to detect one or more dispersive electrodes having a higher current than one or more other dispersive electrodes. Optionally, resistance may be added to one or more dispersive electrodes that have higher currents than one or more other dispersive electrodes. Or, at least one dispersive electrode may be repositioned on the tissue, wherein the at least one dispersive electrode may have a lower current than at least one other dispersive electrode.

Optionally, a method for delivering high-frequency energy may include monitoring current flowing through each of the dispersive electrodes and signaling an alarm when the current through any single dispersive electrode exceeds the current through another dispersive electrode by a predetermined amount. For example, the alarm may be signaled when the current through any single dispersive electrode exceeds a preset amount or exceeds the current through another dispersive electrode by fifteen percent (15%) or more. In another embodiment, an alarm may be activated when the ratio of the highest current (or resistance) to the lowest current (or resistance) exceeds a preset level.

In some embodiments, a method for delivering high-frequency energy includes monitoring the electrical resistance in each of the dispersive electrodes and signaling an alarm when the resistance in any single dispersive electrode exceeds a predetermined maximum resistance. For example, the alarm may be signaled when the resistance in any single dispersive electrode exceeds twenty five ohms (25 Ω), thus signaling improper electrode placement or some other problem.

Optionally, a method for delivering high-frequency energy may further include positioning a third dispersive electrode on human tissue. Alternatively, a third and a fourth dispersive electrode may be positioned on the tissue. Each dispersive electrode may have any suitable conductive surface area. For example, in various embodiments each dispersive electrode may have a conductive surface area of about one hundred twenty square centimeters (120 $cm^2$) or larger.

In some embodiments, a method for delivering high-frequency energy further includes producing analog signals representative of the current flow through each of the dispersive electrodes, converting the analog signals to digital signals, and comparing the digital signals. In one embodiment, a method for delivering high-frequency energy may be used when the target site is a liver in a patient and at least one dispersive electrode is positioned on the right leg of the patient and at least one dispersive electrode is positioned on the left leg of the patient. In various embodiments, a method for delivering high-frequency energy may include delivering total current of at least about one to three amperes (1-3 A).

In yet another aspect, the invention is directed to a method for ablating tissue at a target site wherein at least one subcutaneous active electrode is positioned at the target site beneath a patient's skin and a high-frequency current is established between the subcutaneous active electrode and a dispersive electrode positioned on the patient's skin. One embodiment includes establishing the high-frequency current with at least two dispersive electrodes on the patient's skin and balancing the amount of current passing through each dispersive electrode.

In another aspect, a method for balancing current through two or more dispersive electrodes involves monitoring resistance in each of the dispersive electrodes, comparing resistances in the dispersive electrodes to detect one or more dispersive electrodes having a higher resistance than one or more other dispersive electrodes, and adding resistance to the one or more dispersive electrodes having a lower resistance. In some embodiments, the adding step may include adding resistance across at least two bipolar transistors in series.

In accordance with yet another aspect, the invention is directed to a high-frequency power supply. In preferred embodiments, the power supply generally includes a high-frequency electrical energy source, an active electrode connector for removably attaching the energy source to an active electrode, at least two dispersive connectors for removably connecting at least two dispersive electrodes to the energy source, and current balancing circuitry for balancing current flow from the active electrode through the at least two dispersive electrodes. Optionally, the power supply may also include a monitor for monitoring current flow through the dispersive electrodes and/or an alarm for signaling when the current flow through any single dispersive electrode exceeds the current flow through another dispersive electrode by a predetermined amount.

In some embodiments, the power supply may include a monitor for monitoring resistance through the at least two dispersive electrodes. The power supply may also include an alarm for signaling when the resistance through any single dispersive electrode exceeds a predetermined maximum resistance. The power supply may further include a third dispersive connector for removably connecting a third dispersive electrode, or third and fourth dispersive connectors. In various embodiments, the power supply may be configured for providing total current of at least about one to three amperes (1-3 A).

Other aspects and features of the invention will become apparent from consideration of the following description taken in conjunction with the accompanying drawings.

BRIEF DESCRIPTION OF THE DRAWINGS

The drawings illustrate the design and utility of preferred embodiments of the invention, in which similar elements are referred to by common reference numerals, and in which.

DETAILED DESCRIPTION OF THE ILLUSTRATED EMBODIMENTS

The illustrated embodiments are intended to deliver high-frequency electrical energy to a target tissue site in a patient for performing a monopolar electrosurgical procedure and/or to disperse current flow of the high-frequency energy from the patient. A target tissue site may be located anywhere in a human body and high-frequency energy may be applied to the target tissue for any suitable purpose. For example, various embodiments of the present invention may be used to incise skin and subdermal tissues, to coagulate small blood vessels in any suitable location, and/or to necrose a cancerous tumor, e.g., in a liver, prostate, kidney or other solid organ. High-frequency energy delivered and dispersed by various embodiments of the present invention may include radio frequency energy, microwave energy, and the like.

According to one aspect of the invention, a high-frequency energy source establishes a current flow of high-frequency energy between an active electrode and at least two dispersive electrodes. The energy source also monitors the current flow through the dispersive electrodes and adjusts the current flow through any one of the dispersive electrodes as necessary to balance the current flow through the electrodes By providing relatively balanced current flow through two or more dispersive electrodes, the methods and apparatus of the present invention may prevent unwanted patient burns at the dispersive electrode/skin interfaces.

For the purposes of this application, the terms "dispersive electrode," "patient return electrode," "return electrode," "return pad," and "pad" may refer to a dispersive electrode used to return current from a patient to a high-frequency energy source, such as a RF generator. A patient return electrode typically may include a thin, flexible, adhesive pad, such as the Valleylab™ PolyHesive™ Patient Return Electrode described more fully above, or any other commercially available, proprietary, or not yet conceived device for dispersing current from an active electrode and/or a patient. Furthermore, dispersive electrodes used or incorporated into various embodiments of the present invention may have any suitable size. For example, standard dispersive electrodes often have a conductive surface area of about one hundred twenty square centimeters (120 cm$^2$) or greater. In various embodiments of the invention, however, any suitable size may be chosen for a dispersive electrode.

Figure 1:
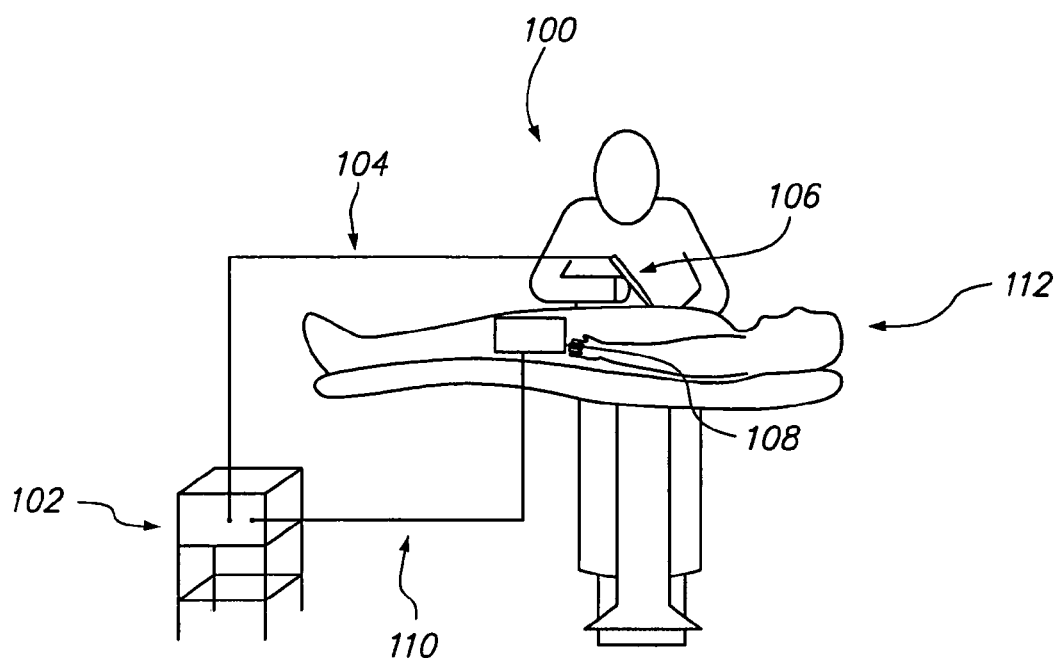
FIG. 1 schematically illustrates a typical system for providing electrosurgery via a monopolar electrosurgical device.

Referring now to FIG. 1, a monopolar electrosurgery system 100 may include a high-frequency electrical energy source 102, an active electrode cable 104, an active electrode 106, a patient 112, a dispersive electrode 108, and a dispersive electrode cable 110. In FIG. 1, only one dispersive electrode 108 and dispersive electrode cable 110 are illustrated, as is common in currently available systems. As is described in more detail below, apparatus and systems of the present invention typically include two, three, four, or more dispersive electrodes and dispersive electrode cables.

In accordance with one aspect of the present invention, energy source 102 is configured to generate a current of high-frequency energy, such as radio frequency (RF) energy, microwave energy, and the like. Active electrode cable 104 may include any device for coupling energy source 102 to active electrode 106 to enable the flow of current from the energy source 102 to the active electrode 106. In various embodiments, the active electrode cable 104 may include wiring or other electrical leads, although alternatively active electrode cable 104 may includes any other elements for enabling current flow between the energy source 102 and the active electrode 106.

In accordance with another aspect of the invention, the active electrode 106 may include any one of a number of currently available or not yet conceived monopolar active electrodes. For example, the active electrode 106 may include a LeVeen™ Needle Electrode or CoAccess™ Electrode, available from Boston Scientific Medi-Tech, as described above. Furthermore, the active electrode 106 may be configured for any suitable function for which monopolar electrodes are used in electrosurgery, such as for cutting tissue, coagulating blood, causing necrosis of cancerous tissue, and the like. For example, the LeVeen™ Needle Electrode or CoAccess™ Electrode is typically used to cause tissue necrosis in cancerous tumors of solid organs, such as cancerous metastases in the liver. Other examples of particular active electrodes are described in U.S. Pat. Nos. 5,868,740, 6,050, 992, and 6,337,998, the disclosures of which are expressly incorporated herein by reference.

Generally, the patient 112 may include any patient upon whom monopolar electrosurgery may be performed. In a typical monopolar electrosurgery procedure, the active electrode 106 is placed on or in the patient 112 at a target tissue site and is used to perform an electrosurgical function on patient tissue, such as ablating, dessicating, coagulating, and/or necrosing.

The dispersive electrode 108 generally includes any device for returning relatively low density current from patient 112, such that the current may then return to the energy source 102. As stated previously, FIG. 1 illustrates only one dispersive electrode 108, whereas various embodiments of the present invention typically include two, three, four, or more dispersive electrodes. The dispersive electrode 108 is configured to have a significantly larger surface area than the active electrode 106, so that current delivered to the patient 112 by the active electrode 106 as high-density current is dispersed from the patient 112 by the dispersive electrode 108 as relatively low-density current. Any suitable dispersive electrode 108 may be used in the electrosurgery system 100. For example, the Valleylab™ PolyHesive™ Patient Return Electrode or any other commercially available dispersive electrode or pad having any suitable conductive surface area may be used.

In accordance with another aspect of the present invention, the dispersive electrode cable 110 may include any component for coupling the dispersive electrode 108 to the energy source 102. Thus, the dispersive electrode cable 110 may include electric wiring or any other suitable connection leads. Just as various embodiments of the electrosurgical system 100 of the present invention typically include multiple dispersive electrodes 108, multiple dispersive electrode cables 110 may also be included.

The electrosurgical system 100 generally includes a circuit. Current generated by the energy source 102 flows through the active electrode cable 104, the active electrode 106, the patient 112, the dispersive electrode 108, and the dispersive electrode cable 110, back to the energy source 102. In accordance with various aspects of the present invention, alterations and additions to the electrosurgical system 100 may be made, without departing from the scope of the invention as set forth in the appended claims. In fact, such alterations and additions may include various aspects of the present invention, as described in further detail below. For example, an electrosurgical system of the present invention may generate and use additional currents, traveling in different directions than the current/circuit described above. Such currents may be used, for example, as interrogation currents to measure a current flow in the dispersive electrodes 108. Additionally, various embodiments may include one or more of the following: three, four, or more dispersive electrodes 108, two, three, four, or more return electrode cables 110, a system for monitoring and adjusting current, an alarm system, and the like. Thus, the foregoing and following descriptions of the electrosurgical system 100 are intended for descriptive purposes of a general system only, and should not be interpreted to limit the scope of the methods, apparatus or systems of the present invention.

To disperse return current flow in monopolar electrosurgery, various embodiments of the present invention may employ one or more different techniques for controlling return current in the dispersive electrodes 108. For example, in one embodiment, current may be controlled by inserting an electronically variable capacitor in series with each dispersive electrode 108. In other embodiments, current may be controlled by inserting an electronically variable inductor or resistor, rather than a capacitor. Such systems may convey certain advantages over other systems for controlling return current. For example, inserting a capacitor or inductor in series with each dispersive electrode 108 would typically not cause significant power loss within the system as a whole. Inserting a capacitor, inductor, or resistor in series, however, may be more difficult to implement than various other systems, due to size requirements, effects of an added variable inductor or capacitor on impedance or power measurements, and the like.

Therefore, in various preferred embodiments of the present invention, dispersive electrode current may be controlled using bipolar transistors (BPTs) or field effect transistors (FETs) as variable resistors in the return path of each dispersive electrode 108. In one embodiment, where alternating current (AC) is applied to the patient 112 via the active electrode 106, two transistors are used for each dispersive electrode 108: one to control positive flow of current and one to control negative flow. The resistance of a bipolar transistor is controlled by the current applied to its base, while the resistance of an FET is controlled by varying the voltage on its gate. By using transistors, an electrosurgical system of the present invention may be configured such that one or more dispersive electrodes 108 may be completely switched out of the circuit. This aspect of the present invention may provide an important safety advantage, allowing startup evaluation of the integrity of the dispersive electrode 108 connections.

Figure 2:
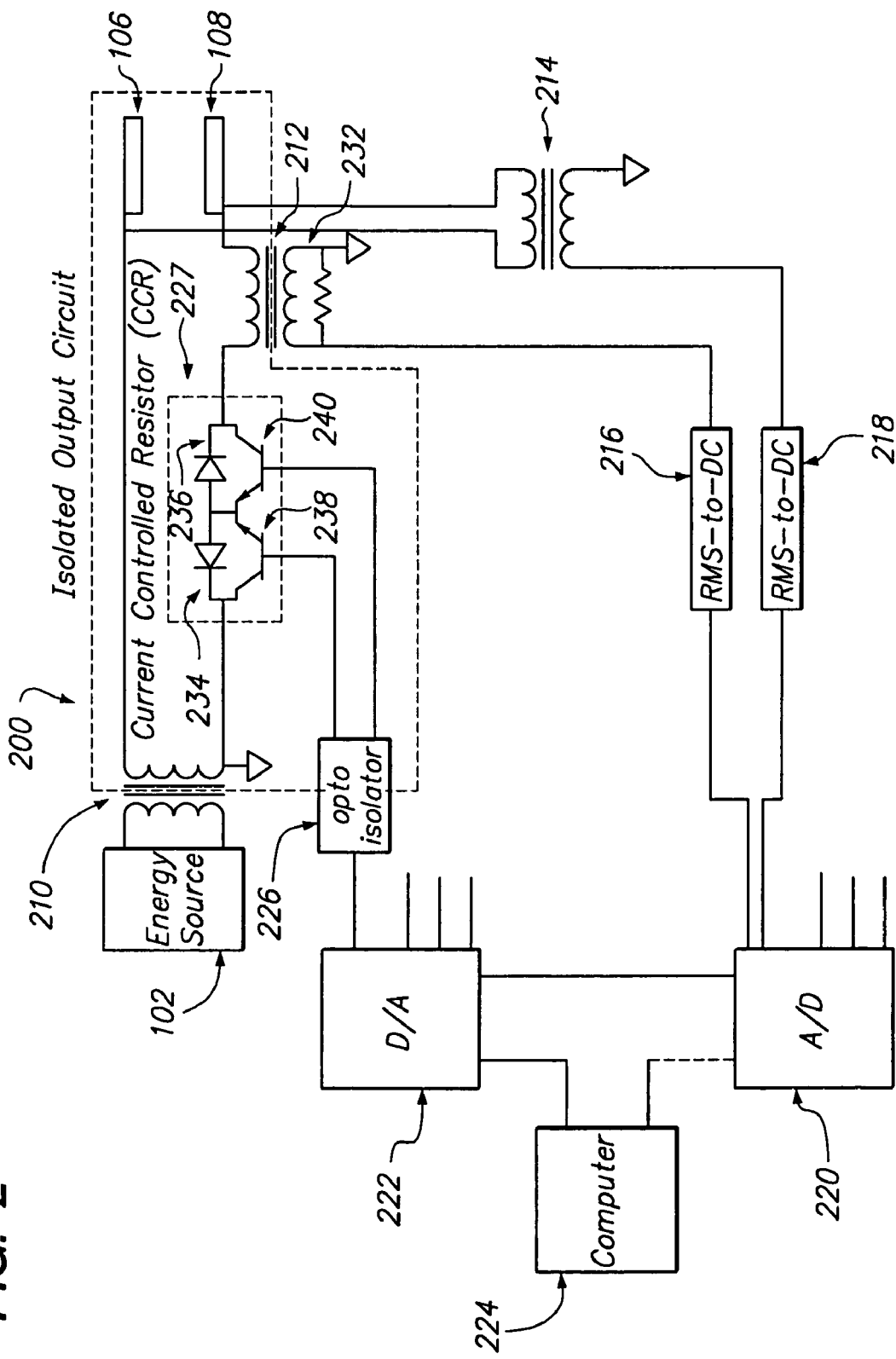
FIG. 2. is a block diagram illustrating one embodiment of a circuit for controlling patient return electrode current according to principles of the present invention.

Referring now to FIG. 2, a circuit 200 for controlling return electrode pad current is schematically illustrated. Although FIG. 2 shows the circuit 200 for controlling pad current including bipolar transistors, other embodiments of the circuit 200 may use FETs or a combination of bipolar transistors and FETs. Furthermore, FIG. 2 illustrates the circuit 200 including only one dispersive electrode 108, while various embodiments of the present invention may include two, three, four, or more dispersive electrodes 108. For the purposes of those embodiments, additional dispersive electrodes 108 may be added to circuit the 200 by repeating a portion of the circuit 200. These embodiments are described more fully below.

According to various aspects of the present invention, the circuit 200 includes energy source 102 and connections to the active electrode 106 and dispersive electrode(s) 108. The circuit 200 may also include three transformers 210, 212, 214, a first resistor 232, multiple additional resistors (not labeled), two root-mean-squared-to-direct-current (RMS-DC) converters 216, 218, an analog/digital (A/D) converter 220, a digital/analog (D/A) converter 222, a computer 224, an isolator 226, and a current controlled resistor (CCR) 227. The CCR 227 may further include a first diode 234, a second diode 236, a first bipolar transistor 238, and a second bipolar transistor 240.

In some embodiments, a first transformer 210 is a high-frequency energy output transformer that couples the energy source 102 to the patient (not shown) and also provides electrical isolation. A third transformer 214 is a voltage-sensing transformer that produces an output voltage proportional to the output voltage of the energy source 102. Output voltage of the third transformer 214 travels to a first RMS-DC converter 218, where the output voltage is converted to DC. The RMS-DC converter 218 may include any suitable RMS-DC converter, such as converters that are currently commercially available or that are developed in the future. From the first RMS-DC converter 218, current travels to a first A/D converter 220, where it is converted to a digital signal that is readable by the computer 224. The computer 224 may include a microcomputer or other device that may read and/or process data from the circuit 200. For example, when the computer 224 reads a value from the first A/D converter 220, the computer 224 may convert that value to the output voltage that is being applied to the patient. Thus, the computer 224 may have access to data representing the output voltage being applied to the patient via the energy source 102 and the active electrode 106.

The RMS-DC converters 216, 218 used in various embodiments of the present invention may be any suitable converters. In one embodiment, Analog Devices AD736 true RMS-to-DC converters may be used, but any other suitable converters may alternatively be used. The RMS-DC converters 216, 218 generally have as part of their circuitry an rms core that performs the operations of squaring, averaging and taking the square root of an input signal to produce as output a DC voltage that represents the RMS value of the input signal. The DC signal output by the RMS-DC converters 216, 218 may then be fed to an input channel of an analog-to-digital (A/D) converter.

Generally, current flows from the active electrode 106, through the patient, through the dispersive electrode 108, then through a second transformer 212. The second transformer 212 is positioned in series between the first resistor 232 and the current controlled resistor (CCR) 227. The second transformer 212 produces a voltage across the first resistor 232 that is proportional to the return electrode current flowing through the primary or second transformer 212. This voltage, in RMS form, travels to a second RMS-DC converter 216, where it is converted to DC voltage. The A/D converter 220 may then convert the current to a digital signal, readable by computer. The computer 224 may read the current value from the A/D converter 220 and convert the value to the value of return electrode current. Thus, the computer 224 may access data representing the current flowing through the dispersive electrode(s) 108.

As high-frequency current is supplied to the active electrode 106 and dispersive electrode 108, the circuit 200 provides information to the computer 224 representing the amount of current flowing through the active electrode 106 and the sum of dispersive electrodes 108. In some embodiments, the computer 224 may compare the amounts of current flowing through the active electrode 106 and the dispersive electrode 108. In one embodiment, for example, the computer 224 may use an algorithm to compare the two current amounts. In accordance with yet another aspect, the computer 224 may then determine an appropriate resistance at the dispersive electrode and, thus, base current that should be applied to bipolar transistors 238, 240. The current is applied to the bases of Q1 and Q2 (of CCR 227) through an optical isolation circuit 226 using a D/A converter 222. Optical isolation circuit 226 is necessary to isolate the patient.

The optical isolation circuit 226 generally produces a barrier to voltages from the main side of the circuit from reaching the patient side of the circuit. This is accomplished by converting an electric current into an infrared light with an infrared LED, passing the light through a light-conducting but electrically non-conducting barrier, and converting it back to an electrical signal with a photo diode. One example of an optical isolation circuit 226 includes a linear optocoupler, such as the IL300 optocoupler (available from Siemens) or any other suitable optocoupler. In one embodiment, an operational amplifier at the circuit input is used to drive the LED. A feedback photodiode sources current to a resistor connected to an inverting input of the operational amplifier. The photocurrent may be directly proportional to the feedback transfer gain times the LED drive current. The operational amplifier may supply LED current to force sufficient photocurrent to keep the node voltage equal to input voltage.

In one embodiment, the output photodiode is connected to a non-inverting voltage follower amplifier. A photodiode load resistor performs the current-to-voltage conversion. The output amplifier voltage is the product of the output forward gain, the LED current, and photodiode load. Therefore, the overall transfer gain (voltage out/voltage in) becomes the ratio of the product of the output forward gain, the photodiode load resistor to the product of the feedback transfer gain, and the input resistor. The overall transfer gain is completely independent of the LED forward current. The optocoupler transfer gain is expressed as the ratio of the output gain to the feedback gain. This shows that the circuit gain becomes the product of the optocoupler transfer gain and the ratio of the output-to-input resistors.

Generally, bipolar transistors 238, 240 may act as switches and/or variable resistors. They act as switches when they are turned fully on or off, and they act as variable resistors when they are turned partially on. In some embodiments, the bipolar transistors 238, 240 may act as switches to switch the return pads 108 in or out of the circuit and as variable resistors to control current flow in the return pads 108.

In accordance with yet further aspects of the invention, the CCR 227 may be configured to act as a switch and a resistor. Initially, the CCR 227 acts as a switch, turning on pads one at a time so that resistance can be estimated. During an ablation procedure, the CCR 227 in each pad acts as a resistor and is used to balance the current in the pads by adding resistance to the pads with the highest currents. The added resistance in pads with the highest currents shifts current to pads with lower currents. When the voltage applied to the patient through the active electrode 106 is positive, the second bipolar transistor 240 is turned on and current flows through the second bipolar transistor 240 and the first bipolar transistor 234. When the voltage applied to the patient through active electrode 106 is negative, the first bipolar transistor 238 is turned on and current flows through the first bipolar transistor 238 and second diode 236. When no base current is applied to either the first bipolar transistor 238 or the second bipolar transistor 240, both transistors are turned off and the CCR 227 acts as an open switch, allowing no current to flow through its associated dispersive electrode 108.

As discussed previously, various embodiments of systems and methods of the present invention may include circuits such as the circuit 200, but may include two, three, four, or more dispersive electrodes 108. According to one aspect of the invention, in order to add one or more dispersive electrodes 108 to the circuit 200, certain components of the circuit 200 are simply duplicated for each additional dispersive electrode 108. For example, in one embodiment, additional dispersive electrodes are added by duplicating dispersive electrode 108, first bipolar transistor 238, second bipolar transistor 240, first diode 234, second diode 236, second transformer 212, first resistor 232, optical isolator 226, and second RMS-DC converter 216.

Figure 3:
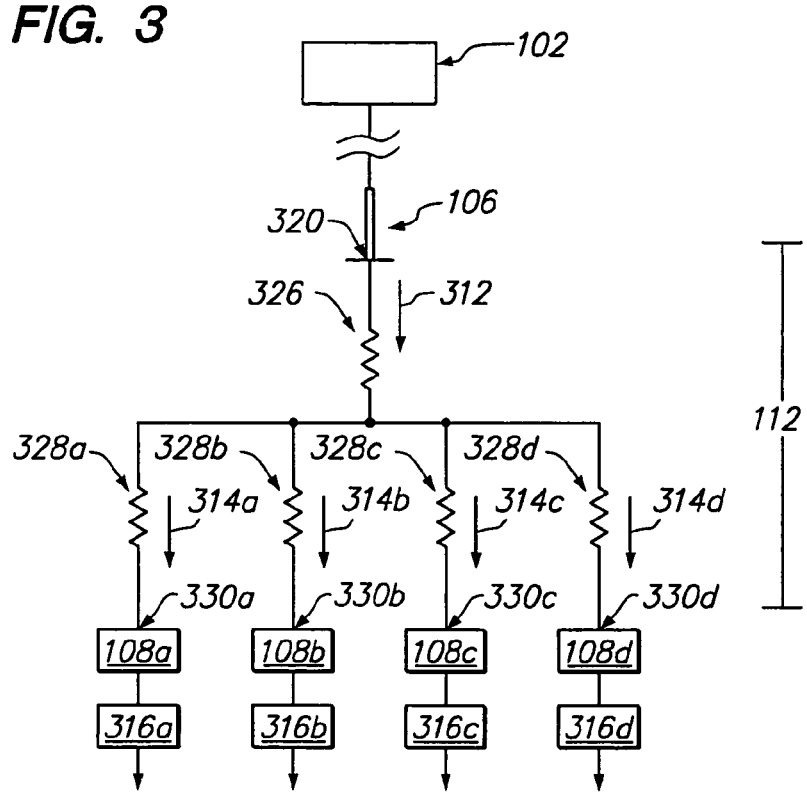
FIG. 3. illustrates an electrical model of one embodiment of a system for providing electrosurgery according to principles of the present invention.

Referring now to FIG. 3, a resistor network 300 illustrates an electrical interaction between the energy source 102 and the patient 112, in an embodiment including four dispersive electrodes 108a-d. According to one aspect of the present invention, voltage is applied to the patient 112 through the active electrode 106, causing an initial current 312 to flow through patient 112. Initial current 312 separates into four divided currents 314a-d as current flows through the patient 112 towards dispersive electrodes 108a-d. After being dispersed from the patient 112, through the dispersive electrodes 108a-d, current flows through the CCRs 316a-d and then back to the energy source 102.

The total patient component of the resistance ($R_P$) represents the electrical resistance at the active electrode/patient interface 320, plus the common 326 and divided 328a-d current path resistances between the active electrode-tissue interface 320 and the dispersive electrodes 108a-d. The total dispersive electrode component of the resistance ($R_E$) represents the electrical resistances at each dispersive electrode/patient interface 330a-d, plus the resistances through each dispersive electrode 108a-d. Typically, $R_P$ may account for the majority of the total voltage drop for the resistor network 300. Because the resistances at the dispersive electrode/patient interfaces 330a-d are typically relatively small, those resistances may be estimated using resistances 328a-d. For example, if the energy source 102 is used for a liver ablation and two dispersive electrodes are placed on the patient, one on corresponding positions of each thigh, current may flow from the active electrode, through the torso and then separate, flowing down the two legs to the two dispersive electrodes. The resistances in the legs may be essentially the same and may be included in the common resistance, leaving the dispersive electrode/patient interface resistance and a small resistance representing the variation in resistance between the two legs.

Current controlled resistors (CCRs) 316a-d are generally configured to connect the dispersive electrodes 108a-d to the energy source 102, completing the circuit 200 (FIG. 2). The resistances of the CCRs 316a-d may be varied to switch one or more of the dispersive electrodes 108a-d in or out of the circuit 200 and, additionally, to balance the currents amongst the dispersive electrodes 108a-d.

A monopolar electrosurgery system as described by FIGS. 2 and 3 may be used to balance current among multiple dispersive electrodes 108a-d. If multiple dispersive electrodes 108a-d are all correctly applied to the patient 112 such that relatively sound and equal dispersive electrode/patient interface 330a-d are created, there will generally be a low contact resistance at each interface 330a-d. In that case, balancing current between the dispersive electrodes 108a-d may compensate for electrode location and orientation to reduce the potential for a burn. For example, if two dispersive electrodes are placed on the same leg, one proximal to the other, the physical positions may dictate that the proximal electrode carry higher current, unless the system balances the currents in some manner. Current balancing may correct for such a placement of the dispersive electrodes.

In a different example, one or more dispersive electrodes 108a-d may be misapplied to the patient 112. For example, one dispersive electrode 108a may be accidentally folded under the patient, so that the electrode pad has only half its normal surface area. In that case, the misapplied electrode 108a may carry a lower current, unless the system balanced the currents. Balancing the currents in this situation, however, may force more current through the misapplied dispersive electrode 108a, which may typically cause heating and possibly burning of the patient's skin at the dispersive electrode/patient interface 320a.

Figure 4:
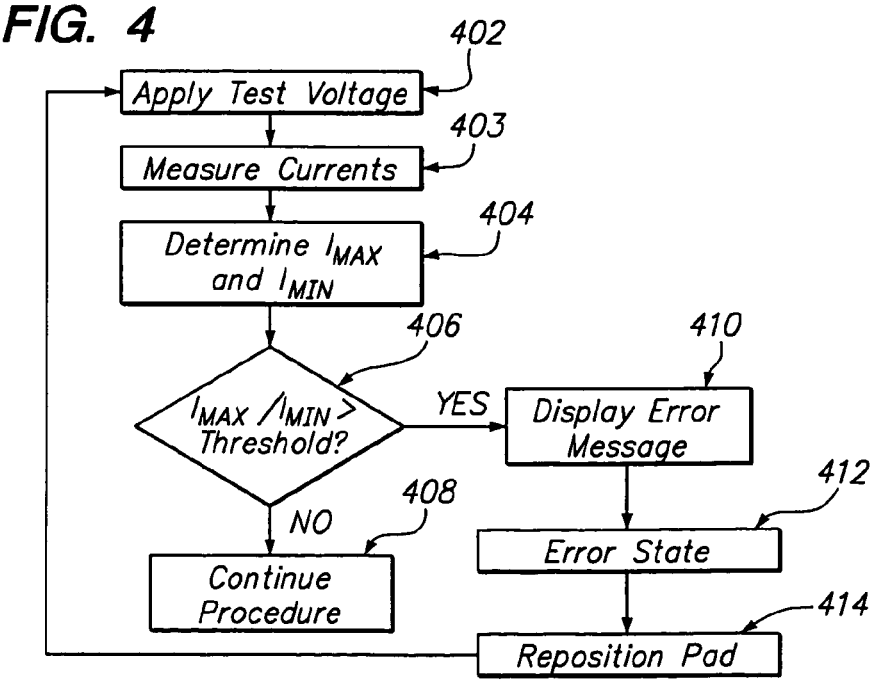
FIG. 4. is a flowchart illustrating one embodiment of a dispersive electrode integrity check using dispersive electrode currents, according to principles of the present invention.

Therefore, various embodiments of the present invention provide for current balancing amongst dispersive electrodes 108a-d and also provide for testing the integrity of the dispersive electrodes 108a-d. Such testing may be performed before or during an electrosurgical procedure, by multiple suitable methods. Referring now to FIG. 4, in various embodiments a test of dispersive electrodes involves comparing electrode currents. A test begins by applying a small test voltage 402 to the patient. Currents are then measured 403 in each of the dispersive electrodes 108a-d (using circuitry as described in FIG. 2), and the maximum current ($I_{max}$) and minimum current ($I_{min}$) for electrodes 108a-d may be determined 404. A ratio of $I_{max}/I_{min}$ may then be calculated and compared to a predetermined threshold level 406. If a predetermined threshold current level is not exceeded, the system is enabled to continue the electrosurgical procedure. If the predetermined threshold current is exceeded, the system may display an error message 410 (for example, on a small screen incorporated into the high-frequency energy source). For example, an error message may indicate that an error in the system has occurred and may indicate which dispersive electrode(s) 108a-d may have currents, causing the ratio to exceed the threshold. When an error exists, the system may also switch to an "error state" 412. To remove the system from the error state and continue with an electrosurgical procedure, an operator of the system must properly place or replace 414 the high or low dispersive electrode(s) 108a-d and retest the system 402.

Figure 5:
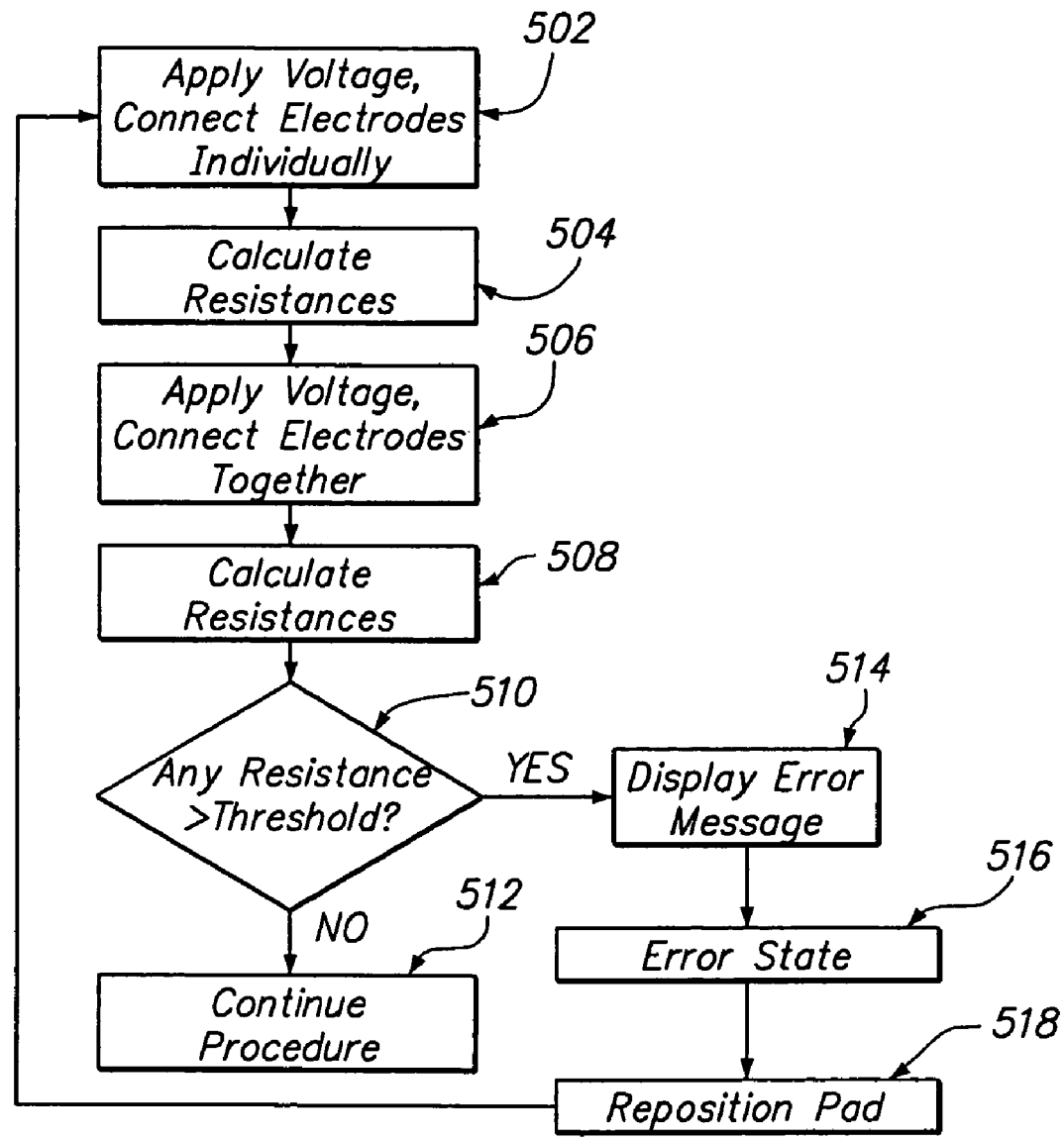
FIG. 5 is a flowchart illustrating one embodiment of a dispersive electrode integrity check using dispersive resistance, according to principles of the present invention.

Referring now to FIG. 5, other various embodiments may test dispersive electrode integrity using electrode resistances. Such testing involves estimating resistance at each dispersive electrode 108a-d by switching the electrodes 108a-d in and out of the circuit 200 (FIG. 2). First, a small test voltage is applied to the patient, each dispersive electrode 108a-d is connected individually, one at a time 502, and a resistance for each dispersive electrode 108a-d is calculated 504. Then another small test voltage is applied. When all of the dispersive electrodes 108a-d are connected simultaneously 506, individual and total resistances may be calculated 508. Individual dispersive electrode 108a-d resistance values may then be compared to a predetermined threshold value 510. If no individual dispersive electrode 108a-d resistance exceeds the threshold, the system enables an electrosurgical procedure to continue 512. If any individual dispersive electrode 108a-d resistance exceeds the threshold, the system may display an error message 514, as described above with reference to FIG. 4. The system may also switch to error state 516 and not allow an electrosurgical procedure to continue until the high resistance dispersive electrode is repositioned 518 or fixed and the test is performed again 502.

Figure 6:
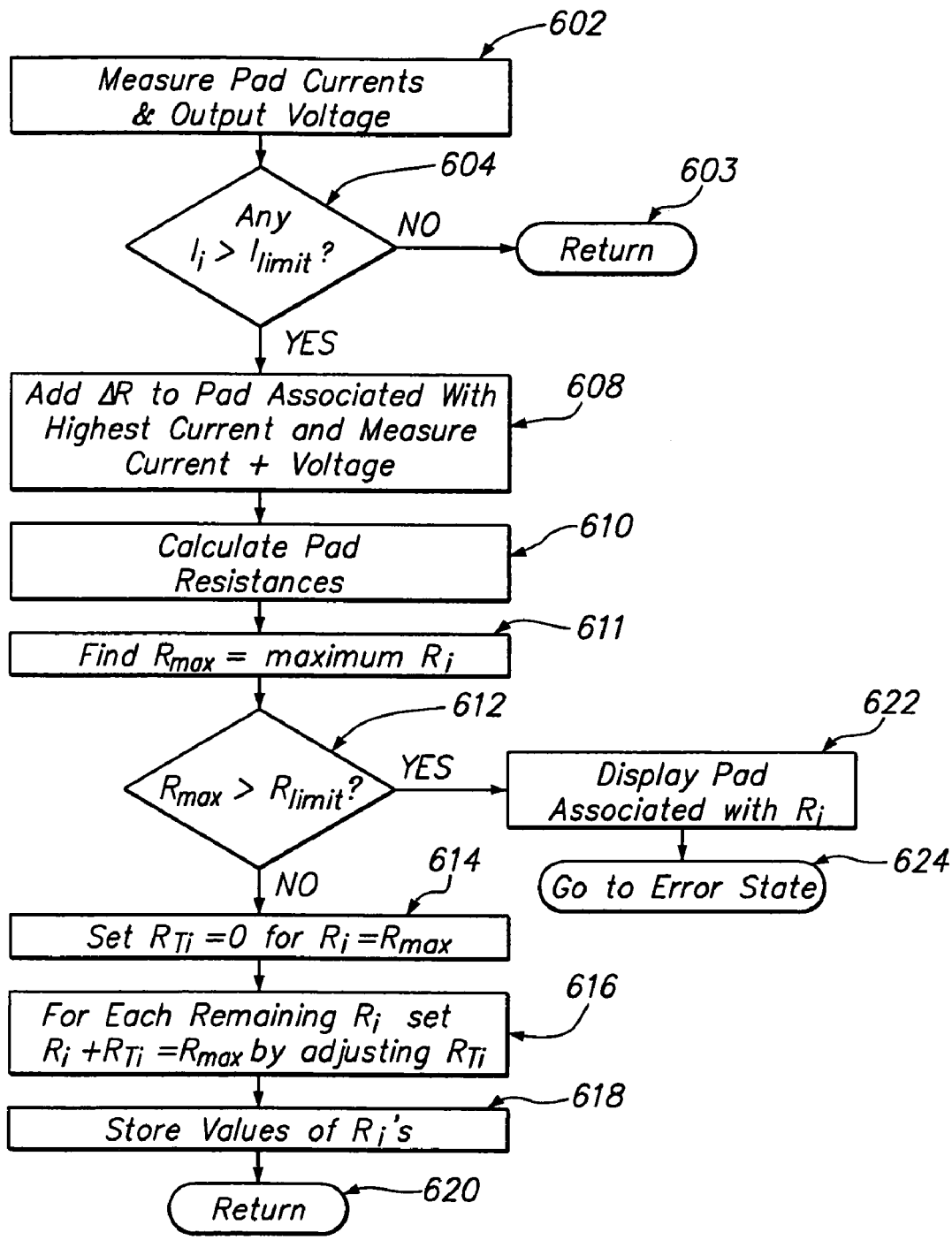
FIG. 6 is a flowchart illustrating one embodiment of a method for balancing dispersive electrode current, according to principles of the present invention.

According to another aspect of the present invention, in addition to measuring currents and/or resistances in the dispersive electrodes 108a-d, a method for balancing currents amongst the dispersive electrodes 108a-d is provided. Referring now to FIG. 6, a method for balancing current suitably begins by measuring currents in the dispersive electrodes 108a-d and output voltage from the energy source 602. A comparison is then made to determine if any individual current $I_i$ exceeds a predetermined current limit $I_{LIMIT}$. If no current exceeds the limit, the system may return 603 to operating mode for continuing an electrosurgical procedure. If any individual current exceeds the predetermined limit, a small, predetermined amount of resistance may then be added to the dispersive electrode 108a-d that has the least resistance (and therefore carries the highest current), and then current and voltage may again be measured 608.

Resistances for the dispersive electrodes 108a-d may then be calculated 610, the maximum resistance may be calculated 611, and a determination may be made whether the maximum resistance in a single dispersive electrode 108a-d exceeds a predetermined limit 612. If so, an error message may be displayed 622, and the system may enter error state 624. If not, then the CCR resistance associated with the maximum pad resistance (Rmax) may be set to zero 614, and the remaining pad resistances plus their associated CCR resistances may be set to Rmax by adjusting the CCR resistances 616. Typically, the appropriate base voltages may be either calculated using a lookup table or an equation. In this way, currents in the dispersive electrodes 108a-d may be balanced. The individual resistances for the dispersive electrodes 108a-d may then be stored and the system may return to operational mode to enable an electrosurgical procedure to continue.

Generally, the current balancing method just described in terms of FIG. 6 may balance the current in the four dispersive electrodes 108a-d by adding resistance to three of them. This equalizes the current in the dispersive electrodes 108a-d, bringing the amount of individual current closer together and, thus, minimizing the potential for a patient burn. In other embodiments of the present invention, an alternative method may include adding resistance to the pad with the highest current to bring the current below a predetermined maximum current. Embodiments using such methods may be advantageous in that they may prevent current in the dispersive electrodes 108a-d from exceeding a predetermined maximum level without requiring significant additional power from the high-frequency energy source.

Figure 7:
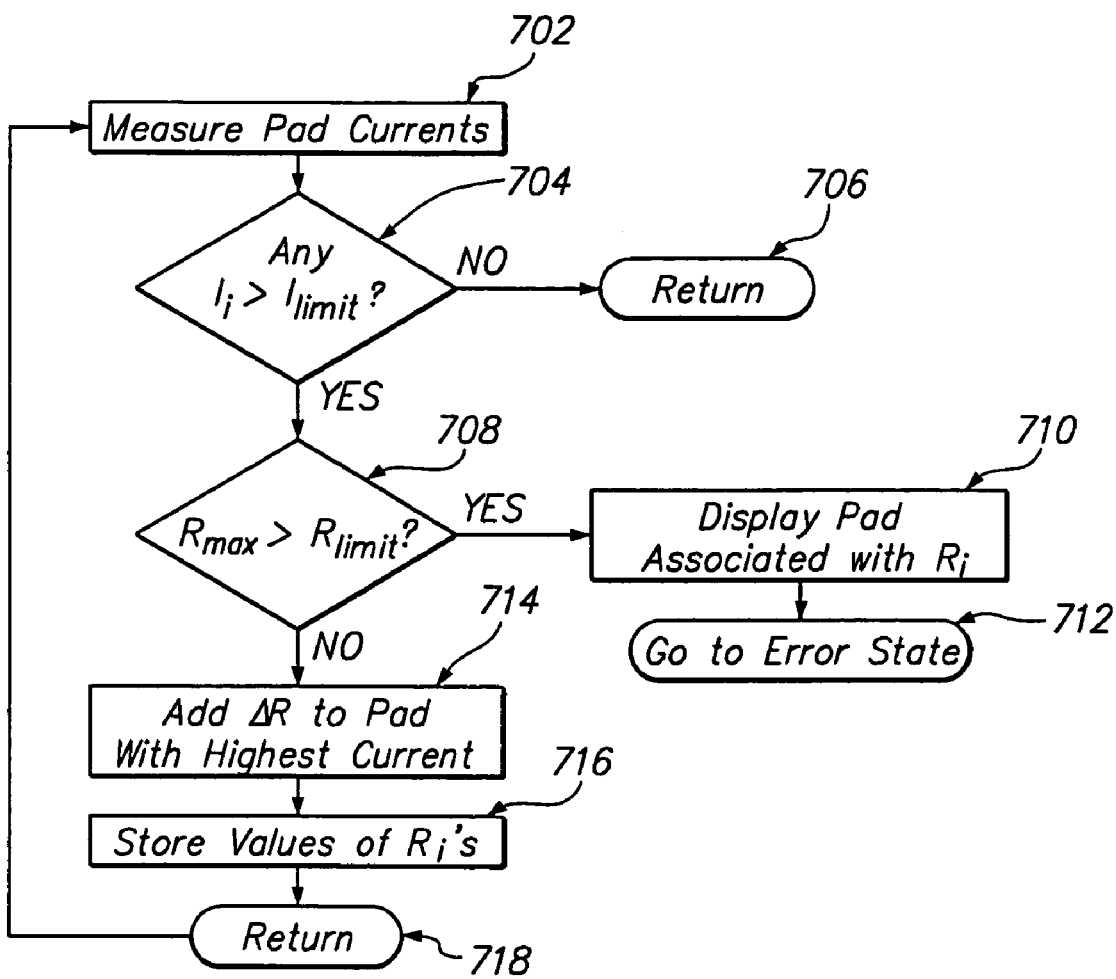
FIG. 7 is a flowchart illustrating one embodiment of a method for balancing dispersive electrode current by adding resistance to a high-current electrode, according to principles of the present invention

In other various embodiments of the present invention, yet another method may be used to balance current in the dispersive electrodes 108a-d. Referring now to FIG. 7, a method for balancing current may include measuring current 702 in the dispersive electrodes 108a-d and determining whether any individual current exceeds a predetermined current maximum 704. If not, the system may remain in normal functioning mode 706. If an individual current does exceed the maximum, a determination may be made whether the maximum resistance in any individual dispersive electrode 108a-d exceeds a predetermined maximum resistance 708. If so, an error message may be displayed 710 and the system may enter error mode 712. If not, a small, predetermined amount of resistance may be added to the dispersive electrode 108a-d with the highest current 714 and the values of the individual dispersive electrode resistances may be stored 716. The system may then return to normal operational mode 718, pad current may be measured again 702, and the process repeated, until the current in each dispersive electrode 108a-d is brought below the predetermined maximum current.

Although preferred embodiments of the invention are shown and described herein, it would be apparent to those skilled in the art that many changes and modifications may be made thereto without the departing from the scope of the invention, which is defined by the appended claims.

What is claimed:

1. A high-frequency power supply, comprising:
   an electrical energy source;
   an active electrode connector for removably attaching an active electrode to the energy source;
   a plurality of dispersive connectors for removably connecting a plurality of dispersive electrodes to the energy source; and
   current balancing circuitry capable of balancing current from the active electrode through the dispersive electrodes,
   wherein the current balancing circuitry comprises:
   a current controlled resistor (CCR) for each of the dispersive electrodes; and
   a computer for transmitting signals to each CCR to vary the resistance to the respective dispersive electrode.

2. A high-frequency power supply as in claim 1, wherein the current balancing circuitry further comprises a monitor for monitoring individual current through each of the dispersive electrodes.

3. A high-frequency power supply as in claim 2, wherein the computer is for comparing the current through each of the dispersive electrodes.

4. A high-frequency power supply as in claim 3, wherein the computer is for adding resistance to one or more of the plurality of dispersive electrodes that have higher current than one or more others of the plurality of dispersive electrodes.

5. A high-frequency power supply as in claim 3, wherein the monitor is for producing analog signals representative of the current through each of the dispersive electrodes, the current balancing circuitry further comprises an analog-to-digital (D/A) converter for converting the analog signals to digital signals, and the computer is for comparing the current through each of the dispersive electrodes based on the digital signals.

6. A high-frequency power supply as in claim 2, wherein the current balancing circuitry further comprises an alarm for signaling when the current through any single dispersive electrode exceeds the current through another dispersive electrode by a predetermined amount.

7. A high-frequency power supply as in claim 6, wherein the alarm is for signaling when the current through the any single dispersive electrode exceeds the current through the other dispersive electrode by fifteen percent (15%) or more.

8. A high-frequency power supply as in claim 1, wherein the current balancing circuitry further comprises a monitor for monitoring individual resistance through each of the dispersive electrodes.

9. A high-frequency power supply as in claim 8, wherein the computer is for comparing resistances through the dispersive electrodes to detect one or more of the dispersive electrodes having a higher resistance than one or more others of the dispersive electrodes.

10. A high-frequency power supply as in claim 9, wherein the computer is for adding resistance to one or more of the dispersive electrodes that have lower resistances than one or more others of the dispersive electrodes.

11. A high-frequency power supply as in claim 8, wherein the current balancing circuitry further comprises an alarm for signaling when the resistance through any single dispersive electrode exceeds twenty-five ohms.

12. An electrosurgical system comprising:
    an active electrode;
    a plurality of dispersive electrodes; and
    a high-frequency power supply including an electrical energy source coupled between the active electrode and the dispersive electrodes, and current balancing circuitry capable of balancing current from the active electrode through the dispersive electrodes,
    wherein the current balancing circuitry comprises:
    a current controlled resistor (CCR) for each of the dispersive electrodes; and
    a computer for transmitting signals to each CCR to vary the resistance to the respective dispersive electrode.

13. An electrosurgical system as in claim 12, wherein the current balancing circuitry further comprises a monitor for monitoring individual current through each of the dispersive electrodes.

14. An electrosurgical system as in claim 13, wherein the computer is for comparing the current through each of the dispersive electrodes.

15. An electrosurgical system as in claim 14, wherein the computer is for adding resistance to one or more of the plurality of dispersive electrodes that have higher current than one or more others of the plurality of dispersive electrodes.

16. An electrosurgical system as in claim 14, wherein the monitor is for producing analog signals representative of the current through each of the dispersive electrodes, the current balancing circuitry further comprises an analog-to-digital (D/A) converter for converting the analog signals to digital signals, and the computer is for comparing the current through each of the dispersive electrodes based on the digital signals.

17. An electrosurgical system as in claim 13, wherein the current balancing circuitry further comprises an alarm for signaling when the current through any single dispersive electrode exceeds the current through another dispersive electrode by a predetermined amount.

18. An electrosurgical system as in claim 17, wherein the alarm is for signaling when the current through the any single dispersive electrode exceeds the current through the other dispersive electrode by fifteen percent (15%) or more.

19. An electrosurgical system as in claim 12, wherein the current balancing circuitry comprises a monitor for monitoring individual resistance through each of the dispersive electrodes.

20. An electrosurgical system as in claim 19, wherein the computer is for comparing resistances through the dispersive electrodes to detect one or more of the dispersive electrodes having a higher resistance than one or more others of the dispersive electrodes.

21. An electrosurgical system as in claim 20, wherein the computer is for adding resistance to one or more of the dispersive electrodes that have lower resistances than one or more others of the dispersive electrodes.

22. An electrosurgical system as in claim 19, wherein the current balancing circuitry further comprises an alarm for signaling when the resistance through any single dispersive electrode exceeds twenty-five ohms.

23. An electrosurgical system as in claim 12, wherein each of the dispersive electrodes has a conductive surface area of at least one hundred twenty square centimeters (120 cm$^2$).

24. A method for operating a high-frequency power supply as in claim 12, the method comprising:
    positioning the active electrode in or on tissue at a target site;
    positioning the dispersive electrodes on tissue at sites remote from the target site;
    operating the electrical energy source to establish electrical current flow from the active electrode through each of the dispersive electrodes; and
    operating the computer to transmit a signal to at least one of the CCRs to adjust the resistance to the respective dispersive electrode to balance the current through the dispersive electrodes.

25. A method as in claim 24, further comprising:
    monitoring resistance through each of the dispersive electrodes; and
    comparing resistances through the dispersive electrodes to detect one or more of the dispersive electrodes having a higher resistance than one or more others of the dispersive electrodes.

26. A method as in claim 25, further comprising adding resistance to the one or more others of the dispersive electrodes.

27. A method as in claim 24, further comprising:
    monitoring current in each of the dispersive electrodes; and
    comparing current in the dispersive electrodes to detect one or more of the dispersive electrodes having a higher current than one or more others of the dispersive electrodes.

28. A method as in claim 27, further comprising adding resistance to the one or more dispersive electrodes.

29. A method as in claim 24, further comprising monitoring the current through each of the dispersive electrodes and signaling an alarm when the current through any single dispersive electrode exceeds the current through another dispersive electrode by a predetermined amount.

30. A method as in claim 29, wherein the alarm is signaled when the current through any single dispersive electrode exceeds the current through another dispersive electrode by fifteen percent (15%) or more.

31. A method as in claim 29, further comprising monitoring the electrical resistance in each of the dispersive electrodes and signaling an alarm when the resistance in any single dispersive electrode exceeds a predetermined maximum resistance.

32. A method as in claim 31, wherein the alarm is signaled when the resistance in any single dispersive electrode exceeds twenty five ohms.

33. A method as in claim 24, further comprising producing analog signals representative of the current through each of the dispersive electrodes, converting the analog signals to digital signals, and comparing the digital signals.

34. A method as in claim 24, wherein the target site is a liver in a patient and wherein at least one of the dispersive electrodes is positioned on the right leg of the patient and at least one other of the dispersive electrodes is positioned on the left leg of the patient.

35. A method for operating a high-frequency power supply as in claim 12, the method comprising:
    positioning the active electrode in or on tissue at a target site;
    positioning the dispersive electrodes on tissue at sites remote from the target site;
    operating the electrical enemy source to establish electrical current flow from the active electrode through each of the dispersive electrodes;
    monitoring resistance through each of the dispersive electrodes;
    comparing resistances through the dispersive electrodes to detect one or more of the dispersive electrodes having a higher resistance than one or more others of the dispersive electrodes; and
    repositioning the one or more of the dispersive electrodes having the higher resistance.

36. A method for operating a high-frequency power supply as in claim 12, the method comprising:
    positioning the active electrode in or on tissue at a target site;
    positioning the dispersive electrodes on tissue at sites remote from the target site;
    operating the electrical enemy source to establish electrical current flow from the active electrode through each of the dispersive electrodes;
    monitoring current in each of the dispersive electrodes;
    comparing current in the dispersive electrodes to detect one or more of the dispersive electrodes having a higher current than one or more others of the dispersive electrodes; and
    repositioning the one or more others of the dispersive electrodes.

* * * * *

UNITED STATES PATENT AND TRADEMARK OFFICE
CERTIFICATE OF CORRECTION

PATENT NO. : 7,566,332 B2
APPLICATION NO. : 10/705166
DATED : July 28, 2009
INVENTOR(S) : Jarrard et al.

Page 1 of 1

It is certified that error appears in the above-identified patent and that said Letters Patent is hereby corrected as shown below:

Col. 13, Claim 1, Line 38 replace "capable of" with -- for --

Col. 14, Claim 12, Line 31 replace "capable of" with -- for --

Col. 16, Claim 35, Line 28 replace "enemy" with -- energy --

Col. 16, Claim 36, Line 45 replace "enemy" with -- energy --

Signed and Sealed this

First Day of December, 2009

David J. Kappos
*Director of the United States Patent and Trademark Office*